(12) United States Patent
Yagi et al.

(10) Patent No.: US 9,651,570 B2
(45) Date of Patent: May 16, 2017

(54) AUTOMATIC CENTRIFUGE, PRE-ANALYSIS SYSTEM WITH AUTOMATIC CENTRIFUGE AND THE CONTROL TECHNIQUES OF THAT SYSTEM

(75) Inventors: Kenichi Yagi, Hitachinaka (JP);
Takayuki Noda, Hitachinaka (JP);
Masashi Akutsu, Hitachinaka (JP)

(73) Assignee: Hitachi High-Technologies Corporation, Tokyo (JP)

(*) Notice: Subject to any disclaimer, the term of this patent is extended or adjusted under 35 U.S.C. 154(b) by 272 days.

(21) Appl. No.: 13/976,672

(22) PCT Filed: Dec. 20, 2011

(86) PCT No.: PCT/JP2011/079560
§ 371 (c)(1),
(2), (4) Date: Jun. 27, 2013

(87) PCT Pub. No.: WO2012/090795
PCT Pub. Date: Jul. 5, 2012

(65) Prior Publication Data
US 2013/0281279 A1    Oct. 24, 2013

(30) Foreign Application Priority Data

Dec. 28, 2010  (JP) ................................. 2010-291532

(51) Int. Cl.
*B04B 9/14*       (2006.01)
*G01N 35/04*      (2006.01)
*B04B 11/04*      (2006.01)

(52) U.S. Cl.
CPC ............. *G01N 35/04* (2013.01); *B04B 9/146* (2013.01); *B04B 2011/046* (2013.01)

(58) Field of Classification Search
CPC ..... B04B 9/14; B04B 9/146; B04B 2009/143; B04B 2011/046; G01N 35/02; G01N 35/04; G01N 35/025; G01N 35/026
(Continued)

(56) References Cited

U.S. PATENT DOCUMENTS 5,769,775 A * 6/1998 Quinlan et al. .................. 494/10
5,898,169 A * 4/1999 Nordbryhn ................ 250/223 B
(Continued)

FOREIGN PATENT DOCUMENTS

EP    0629858 A1 * 12/1994 ........... G01N 35/026
GB    9505766    * 5/1995  ......... G01B 11/2433
(Continued)

*Primary Examiner* — Walter D Griffin
*Assistant Examiner* — Shirley S Liu
(74) *Attorney, Agent, or Firm* — Mattingly & Malur, PC

(57) ABSTRACT

A determination mechanism which obtains information about the weight of the specimen housed in the specimen container is arranged on a conveyor line for connecting between a loading module and an automatic centrifugal unit, the specimens are held without being installed at an adaptor until the number of the specimens which can be subjected to a centrifugal processing at once by the automatic centrifugal unit arrives, and the specimens are installed after the arrival in an order from a heavier specimen at the adaptors to be paired, which are installed at the symmetric positions to each other across the rotation central axis. Also, the specimen is installed at the gravity-center position of the adaptor first, and the subsequent specimens are installed from the inner side at the point-symmetric positions to each other across the gravity-center position.

19 Claims, 7 Drawing Sheets

(58) Field of Classification Search
USPC .................................................... 494/1, 42
See application file for complete search history.

(56) References Cited

U.S. PATENT DOCUMENTS

| | | | |
|---|---|---|---|
| 6,060,022 A * | 5/2000 | Pang et al. ..................... 422/65 |
| 6,455,002 B1 | 9/2002 | Jokes et al. |
| 6,589,789 B1 * | 7/2003 | Hubert ............... G01N 35/0099 |
| | | | 422/504 |
| 6,678,576 B2 * | 1/2004 | Kiyohara ............... G06Q 10/04 |
| | | | 414/809 |
| 2003/0223916 A1 * | 12/2003 | Testrut ..................... B01L 9/06 |
| | | | 422/400 |
| 2005/0158212 A1 * | 7/2005 | Yavilevich ......... G01N 35/0099 |
| | | | 422/400 |
| 2009/0151474 A1 * | 6/2009 | Mehus et al. ............. 73/862.52 |

FOREIGN PATENT DOCUMENTS

| | | | | |
|---|---|---|---|---|
| JP | 52-92968 A | 8/1977 | | |
| JP | 03-127647 A | 5/1991 | | |
| JP | 4-145968 A | 5/1992 | | |
| JP | 7-80355 A | 3/1995 | | |
| JP | 2000-180454 A | 6/2000 | | |
| JP | 2001-505648 A | 4/2001 | | |
| WO | 98/01760 A2 | 1/1998 | | |
| WO | WO 9801760 * | 6/1998 | ......... G01N 35/0095 |
| WO | WO 2008027569 A2 * | 3/2008 | ............. G01B 11/06 |
| WO | WO 2013070755 A2 * | 5/2013 | ........... B01D 21/262 |

* cited by examiner

FIG. 7

| RANGE VALUE SETTING OF NORMAL SPECIMEN WEIGHT (g) | | |
|---|---|---|
| 100 mm TEST TUBE (16 φ) | 10 | 30 |
| 75 mm TEST TUBE (16 φ) | 7 | 20 |
| 100 mm TEST TUBE (13 φ) | 8 | 25 |
| 75 mm TEST TUBE (13 φ) | 5 | 18 |
| OTHERS | 3 | 40 |

AUTOMATIC CENTRIFUGE, PRE-ANALYSIS SYSTEM WITH AUTOMATIC CENTRIFUGE AND THE CONTROL TECHNIQUES OF THAT SYSTEM

TECHNICAL FIELD

The present invention relates to an automatic centrifuge for performing centrifugal process to a specimen inside a pre-analysis system, and, more particularly, the present invention relates to a pre-analysis system, a specimen-test automation system, and control techniques of the systems capable of avoiding unbalanced operation due to a weight difference upon the centrifugal process.

BACKGROUND ART

In recent years, in the medical field, a labor-saving test operation has been promoted by introducing various automation devices. In tests in a hospital, test specimens of hospital inpatients and outpatients are collected in each department in the hospital, and are collectively processed in a test room. A test item for each specimen is transferred from a doctor to the test room by using an online information processing system, and a result of the test is reversely reported online from the test room to the doctor. Most of test items for blood and urine require pre-analysis processing such as centrifugal processing, decap processing, and dispensing processing as the pre-analysis processing of the test processing, and a rate occupied in the entire test operation time by the operation for them is large.

The centrifugal processing of the pre-analysis processing is a processing for extracting serum components by performing centrifugation to the blood collected from a patient so as to obtain a test sample. Generally, an automatic centrifuge used in a specimen-test automation system has a plurality of bucket groups held by a rotating rotor so as to be swung. Each of the bucket groups is configured of a plurality of pair of buckets, and each of the pair of buckets is configured of buckets positioned rotation-symmetrically to each other across a rotation axis of the rotor. Into each of the buckets, a plurality of (for example, about 5 to 10) specimens are inserted while they are set on an adaptor and are held so as to stand up. Conventionally, the specimens have been inserted into the respective buckets by a human hand. However, an aim of a specimen-test automation system in which the pre-analysis processing is automated is to automate these operations.

The centrifugal operation is performed by rotating the rotor at high speed. Therefore, if weights of the buckets arranged at the pair of buckets are significantly different from each other, the rotation abnormality of the rotor is caused, and the centrifugal operation cannot be normally performed. Therefore, it is required to execute weight adjustment at a prior stage to installation at the rotor.

As to means for this weight adjustment, in Patent Document 1, a weight called dummy rack is used to reduce a weight difference between the buckets. On the other hand, Patent Document 2 discloses a technique in which weights of all racks are previously measured, and they are stocked once, and a pair of racks having a weight difference therebetween within a predetermined amount are selected from a group of the stocked racks and are inserted into the pair of buckets.

Patent Document 2 discloses a technique in which the difference in the weight between the adaptors positioned symmetrically to each other is minimized by providing a specimen-container weight-measurement mechanism in an automatic centrifuge, and repeating to compare total weights of the adaptors (adaptors A and B) with each other placed on a pair of buckets positioned symmetrically to each other across a centrifugal rotation center of a rotor so as to place a next specimen container on the adaptor B if the adaptor A is heavier, conversely, so as to place the next specimen container on the adaptor A if the adaptor B is heavier, and to compare the weights of the adaptors A and B again, until there is no vacant position on either one of the adaptors.

PRIOR ART DOCUMENTS

Patent Documents

Patent Document 1: Japanese Patent Application Laid-Open Publication No. H04-145968
Patent Document 2: Japanese Patent Application Laid-Open Publication No. H07-80355

DISCLOSURE OF THE INVENTION

Problems to be Solved by the Invention

In the technique described in Patent Document 1, the weight installed on the bucket is not measured, and the dummy rack is used only when the numbers of the installed racks are different. Therefore, when test tubes have different sizes from each other so that the weight difference therebetween is large, it is difficult to correctly balance the weights. Moreover, a space for arranging a member such as the dummy rack is also required, and therefore, there is a possibility that a size of the device is increased due to them.

On the other hand, in the technique described in Patent Document 2, all the racks loaded into the device are stocked once, and then, the pair of racks having a small weight difference therebetween is determined. Therefore, the racks cannot be transferred to the buckets in an order of the loading in some cases depending on their combination. Also, if the weights eventually cannot be balanced, it is required to use the dummy rack.

As other techniques, there is a technique of repeating to measure the weight of the specimen container containing the specimen therein by the specimen-container weight-measurement mechanism, to compare the total weights of the symmetrically-positioned adaptors with each other, and to set the specimen container on the lighter adaptor, until there is no vacant position on either one of the adaptors to be paired.

However, in the above-described technique, depending on the difference in the total weight between the adaptors to be paired, if there is no vacant position on either one of the adaptors at which a new specimen container can be installed, the centrifugal processing is executed even if there is a vacant position on the other adaptor. In that case, the number of the specimens which can be subjected to the centrifugal processing at once is reduced, and processing performance is lowered.

Also, even if the difference in the total weight between the adaptors to be paired is minimized, if the weights of the specimen containers are varied, there is a possibility that a position of the gravity center in the adaptors is shifted to cause the rotation abnormality, and therefore, the centrifugal processing cannot be normally performed. For example, it is assumed that many specimen containers each weighing at a position away from the rotation axis of the rotor are set on one adaptor, and assumed that many specimen containers each weighing at a position close to the rotation axis of the rotor are set on the other adaptor configuring the pair of buckets together with the one adaptor. Even if there is no difference in the total weight between the adaptors to be paired, there is a possibility that the rotation abnormality of the rotor of the automatic centrifuge is caused due to the position shift of the gravity center of the adaptors to be paired upon the execution of the centrifugal processing, and therefore, the centrifugal processing is not normally performed.

In addition, if the number of specimens to be conveyed to the automatic centrifuge is small, control is performed so as to execute the centrifugal processing after a certain period of time has passed in many cases even if there is vacancy on the adaptor. At that time, if the setting states of the specimen containers on the respective adaptors are unbalanced, the gravity center in the adaptors is similarly shifted, and this can be similarly a cause of the rotation abnormality of the rotor.

Also, in the technique described in Patent Document 1, when the weight of the specimen container containing the specimen therein is measured by the specimen-container weight-measurement mechanism, the weight together with a holder at which the specimen container is set is measured. Then, the weight of the specimen container is measured by subtracting the weight of the holder from the measured weight.

However, there is a possibility that the weights of the holders are varied due to variation in machining accuracy, secular change caused by usage of the holder for a long period of time, or others, and therefore, the weight of the specimen container cannot be correctly measured in some cases. According to the above description, even if the set destination of the specimen container is determined in the automatic centrifuge based on the measured weight of the specimen container, there is a possibility that the centrifugal operation is affected due to influence of the variation in the weight of the holder.

As the specimen to be loaded into the pre-analysis system, a specimen whose volume is a certain volume or more is required for such a pre-analysis processing as the centrifugal processing and the dispensing processing. However, when a specimen whose volume is less than the certain volume is erroneously loaded into the pre-analysis system, the specimen dispensing is performed from the specimen container, and lack of the specimen is recognized, and then, lack of the specimen volume is finally recognized, and the specimen is conveyed out from the device as the abnormality in the specimen. Then, a user takes such an action as addition of the specimen, and loads the specimen into the device again. However, in this workflow, the recognition of abnormality in the specimen is late, and therefore, report delay of the measurement result is finally extended.

The present invention has been made in consideration of the above-described conventional problems, and a preferred aim thereof is to provide a specimen-test automation system capable of performing normal centrifugal operation and minimizing result report delay of an abnormal specimen without reducing processing performance of an automatic centrifuge by correctly recognizing a weight of a specimen loaded into the specimen-test automation system at a prior stage to conveying of the specimen to a specimen processing unit.

Means for Solving the Problems

Means for achieving a stable centrifugal processing without reducing processing performance will be described below.

In a specimen-test automation system having: a loading module for loading a specimen into a system; a housing module for housing and storing the specimen for which the processing has been completed; a conveyor line for conveying a specimen rack holding at least one specimen container; and a plurality of specimen processing units arranged along the conveyor line, the specimen-test automation system has a feature that a specimen-container weight-measurement mechanism for measuring a weight of the specimen container is arranged on the conveyor line that connects between the loading module and the specimen processing unit. In the specimen-test automation system, for the specimen loaded from the loading module, the weight of the specimen container is measured by the specimen-container weight-measurement mechanism on the conveyor line, and the specimen container is conveyed to the automatic centrifuge. The specimen container conveyed to the automatic centrifuge stands by without being set at an adaptor until the number of specimens which can be subjected to the centrifugal processing at once arrive. After the maximum number of specimens which can be subjected to the centrifugal processing arrive at the automatic centrifuge, if it is assumed that the adaptors placed on a pair of buckets symmetrically positioned to each other across the centrifugal rotation center of a rotor are adaptors A and B, the weights of the adaptors A and B are compared with each other, and the heaviest specimen container among the specimen containers which have not been set yet is set at the adaptor whose total weight is lighter.

FIG. 1 illustrates an example of a setting order of the specimen containers at the adaptor. A technique of setting the specimen containers will be explained with reference to the present drawing. In FIG. 1, an example of an adaptor 210 is illustrated having holes 211 at which nine specimen containers (not shown in Fig. 1) can be set. In the setting at the setting adaptor 210, the container is set at a center 212 of the adaptor first (see (A) in FIG. 1). The center 212 of the adaptor 210 described here refers to a position which is the closest to a gravity-center position of the adaptor 210 and at which the specimen container can be installed. The second specimen container is set at a position close to the center 212 of the adaptor 210(see (B) in FIG. 1). The third specimen container is set at a position which is a point of symmetry across the adaptor center 212 with respect to the second specimen container(see (C) in FIG. 1). When the second and third specimen containers are set, the specimen containers are set on a supporting shaft 01 of the bucket on which the adaptor 210 is set. The arrangement is repeated (see (D) to (H) in FIG. 1) so that the specimen containers are set sequentially from the center 212 of the adaptor 210 (see (I) in FIG. 1). Also in this case, the setting is sequentially performed at a position which is a point of symmetry across the adaptor center 212.

As the above-described technique, the technique in which the specimen containers are installed at the adaptor sequentially in an order from the heavier weight after the maximum number of specimens which can be subjected to the centrifugal processing arrive at the automatic centrifuge has been described. However, if the number of the specimens loaded into the device is small, the setting of the specimen containers at the adaptor may be started sequentially in an order from the heavier weight at a moment when a previously-input timeout period has passed.

Also, even if the specimen-container weight-measurement mechanism is not on the conveyor line, it may be provided inside the automatic centrifuge so as to measure the specimen weight after the specimen is conveyed to the automatic centrifuge.

Since the specimen containers are allocated to the respective adaptors in the order from the heavier specimen container by the present means, the difference in the weight between the adaptors placed on the respective buckets to be paired is minimized, and the sift of the gravity center of the adaptor is minimized because the heavy specimen container is set on an inner side of the adaptor, so that stable centrifugal processing can be achieved.

Another solution technique for performing the stable centrifugal processing without reducing the processing performance for the specimens will be described below.

For the specimen loaded from the loading module, the weight of the specimen container is measured by the specimen-container weight-measurement mechanism on the conveyor line. The adaptors placed on the pair of buckets positioned symmetrically to each other across the centrifugal rotation center of the rotor of the automatic centrifuge are referred to as the adaptors A and B, the weights of the adaptors A and B are compared with each other, and the specimen container is set at the adaptor whose total weight is lighter.

In a state in which the specimen containers are entirely installed at either the adaptor A or the adaptor B so that a specimen container can be set at only the other adaptor, a fact that the weights are unbalanced by setting a next specimen container at the adaptor having vacancy is previously recognized by measuring the weight by the specimen-container weight-measurement mechanism, and the specimen is conveyed so that the above-described specimen container is subjected to the centrifugal processing in a different automatic centrifuge. If the weights of the respective adaptors are not unbalanced, the specimen container is set at the above-described adaptor having the vacancy.

By the present technique, the unequal weight balance between the adaptors to be paired of the automatic centrifuge can be previously prevented, so that the centrifugal processing can be normally performed. Besides, by continuously setting the specimen, by which the unbalance is not caused, at the adaptor having the vacancy, the number of the specimens which can be subjected to the centrifugal processing at once can be increased, so that the reduction in the processing performance can be prevented.

A technique for measuring the correct specimen weight will be described below.

A holder at which no specimen is set is conveyed to the specimen-container weight-measurement mechanism, and a weight of only the holder is measured. A measurement result thereof is stored in a storage medium included in the holder. A storage technique may be a technique in which the holder weight is stored in the holder itself by providing a RFID (radio frequency identification) in the holder or a technique in which, by pasting a bar code on the holder, the bar-code information and the holder weight are stored in a control computer of the specimen-test automation system.

The weight of the holder at which the specimen container is actually set is measured. When the weight of the specimen container is calculated, the weight of the specimen container is obtained by subtracting the previously-measured holder weight from the measured weight.

From the present technique, the weight of the specimen container can be correctly measured by correctly recognizing the weight of each of the holders, and the normal centrifugal processing can be performed by determining a setting destination of the specimen container in the automatic centrifuge based on the correct weight.

A technique of recognizing the abnormal specimen early and conveying it outside the system will be described below.

When the holder at which the specimen container is set is measured by the specimen-container weight-measurement mechanism, it is checked whether or not the measured weight is within a range of a previously-set normal specimen weight. If it is within the range, it is determined that the specimen having a normal volume is contained in the specimen container, and the subsequent pre-analysis processing is performed. However, if it is out of the range of the normal specimen weight, the specimen is regarded as the abnormal specimen, and the specimen is collected to the housing module.

Note that the specimen containers have a different container weight from each other depending on differences in a container diameter and a specimen-container length, and therefore, the range of the normal specimen weight is also different depending on a category of the specimen container. Accordingly, the shape of the specimen container is recognized, the normal specimen weight that matches the shape of the specimen container is selected, and then, it is determined whether the specimen can be used or not. As means for recognizing the shape of the specimen container, for example, a CCD camera may be used.

According to the present means, such abnormality in the specimen that a specimen volume is small can be detected prior to processing in the pre-analysis module, so that the specimen can be early collected. A user takes an action for the abnormal specimen at an early stage, and loads a specimen again into the specimen-test pre-analysis system, so that result report delay can be suppressed at a minimum.

Effects of the Invention

A weight of a specimen loaded into a specimen-test automation system is correctly recognized at a prior stage to conveying to a specimen processing unit, so that normal centrifugal operation can be performed, and result report delay of an abnormal specimen can be minimized.

BRIEF DESCRIPTIONS OF THE DRAWINGS

FIG. 7 is a drawing illustrating a setting screen for a range value of a normal specimen weight of a specimen container.

BEST MODE FOR CARRYING OUT THE INVENTION

Figure 2:
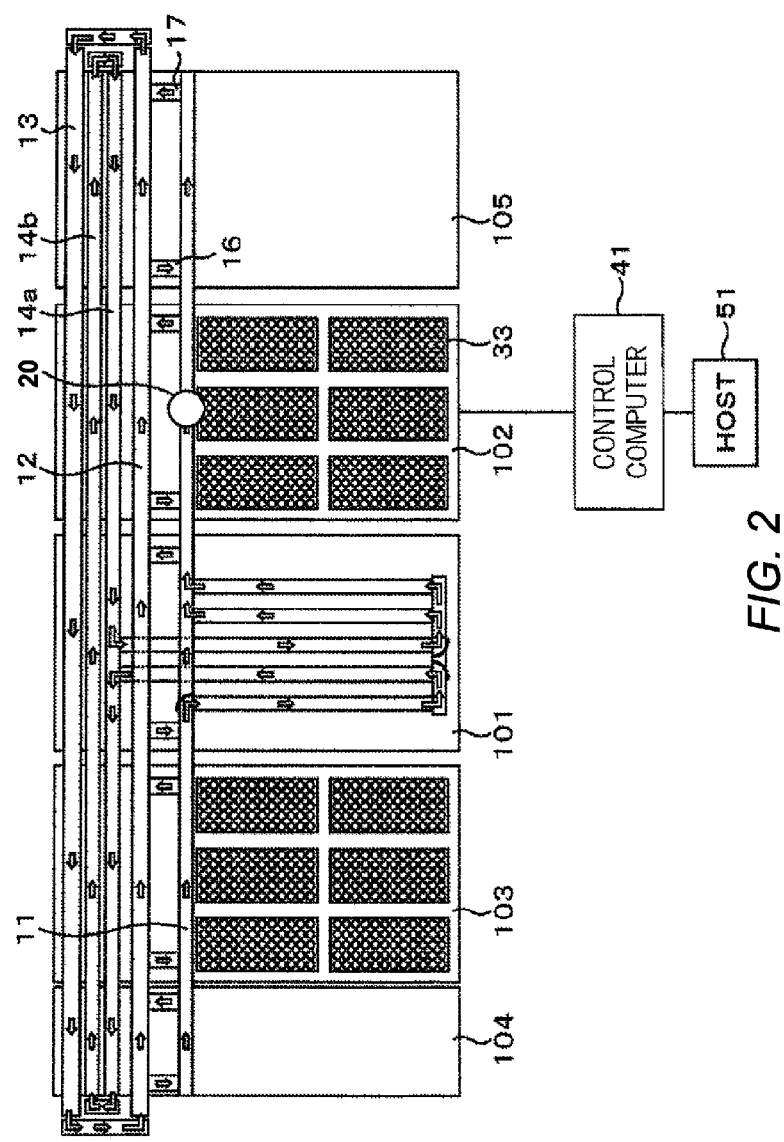
FIG. 2 is an overall diagram according to a specimen-rack conveyor line unit of a specimen-test pre-analysis system.

An overall view related to a specimen-rack conveyor line unit of a specimen-test pre-analysis system according to the present invention is illustrated in FIG. 2.

A holder 31 has a structure in which it can be conveyed on a line while it stands up a specimen container 32 in which body fluid such as blood collected from a patient has been injected, and the holders 31 are provided with unique ID numbers, respectively. The holders 31 convey between respective processing modules by a plurality of conveyor lines which take respective charges of usage. Next, a flow of the specimens in the system will be described.

A tray 33 in which 50 to 100 specimen containers 32 can be installed is installed in a loading module 102. In the loading module 102, the specimen containers 32 in the tray 33 are transferred to the holder 31 by a test-tube chuck mechanism not illustrated. The holders 31 are previously stored in vicinity of an outlet of a rack stocker 101, and the holders 31 are sequentially conveyed to the loading module 102 in accordance with a conveying request made by communication from the loading module 102. After the specimen container 32 is transferred to the holder 31, the bar-code information pasted on the specimen container 32 is read in the loading module 102. The read bar-code information is transferred to a host computer 51, and category information of the specimen which is registered in the host computer 51 is returned to the system.

After the bar-code information is read, a specimen-container weight-measurement mechanism 20 for the weight measurement is arranged on a main conveyor line 11, and total weights of the specimen container 32 and the holder 31 are measured at the position. For each specimen, a result of the total weight measurement is transmitted to a control computer 41 together with an ID number of the holder 31. The control computer 41 determines a processing module by which the holder is to be stopped or a processing module which is to be skipped based on the category information returned from the host computer 51 and the above-described measured specimen weight information, and conveys the specimen container 32 placed on the holder 31 is conveyed to the respective processing modules 104 and 105. The specimen container 32 for which all processing ends is finally conveyed to a housing module 103, and the specimen container 32 is removed from the holder 31 by the test-tube chuck mechanism not illustrated and is housed in the tray 33. The vacant holder 31 from which the holder 31 has been removed is conveyed to the rack stocker 101.

The main conveyor line 11 is a line for conveying the specimen containers 32, which have been loaded into the system, to the respective processing modules.

An emergency overtaking line 12 is a line for making an emergency specimen overtake. And, with the emergency overtaking line 12, the specimen which is not required to stop by the processing module (for example, a specimen which is not required to be centrifuged, or others) can be bypassed by using branch lines 16 and 17 arranged at the respective processing modules.

A return line 13 is a conveyor line for looping (circulating) the specimen containers 32 inside the system. For example, in a case of re-dispensing for a retest or others, the specimen container is looped (circulated) inside the system by using this return line 13.

Vacant-rack conveyor lines 14a and 14b are provided so as to be in parallel to the main conveyor line 11 and so as to have the same line length therewith, and are arranged between the return line 13 and the main conveyor line 11. The state that the vacant-rack conveyor lines 14a and 14b have the same line length as those of the main conveyor line 11 and the return line 13 aims at easiness of the system scalability (addition or reduction of the processing module). More specifically, the aim is to provide an optimum number as the number of vacant racks in accordance with the system scale. The number of vacant racks originally required for the processing in the system is a number thereof by which all of the lines are filled with the holders 31.

In other words, the number of holders more than required for filling all of the lines is unnecessary. When the emergency overtaking line 12 is basically defined so as not to stay the holder 31 but to make the holder pass because of the characteristics thereof, a line length obtained by addition of those of the main conveyor line 11 and the return line 13 is equal to a length obtained by addition of those of the vacant-rack conveyor lines 14a and 14b, and the vacant racks required for the system can be stored in the vacant-rack conveyor lines 14a and 14b. In this manner, the optimum number of vacant holders can be always provided in accordance with the system scale.

Also, in a direction opposite to that of the main conveyor line, this vacant-rack conveyor line 14a conveys the vacant holder which is continuously conveyed from the housing module 103 in order to efficiently collect the vacant holder so that the lines do not cross each other inside the rack stocker 101. Similarly, the vacant-rack conveyor line 14b also conveys the vacant holder in a direction opposite to that of the return line 13.

Figure 3:
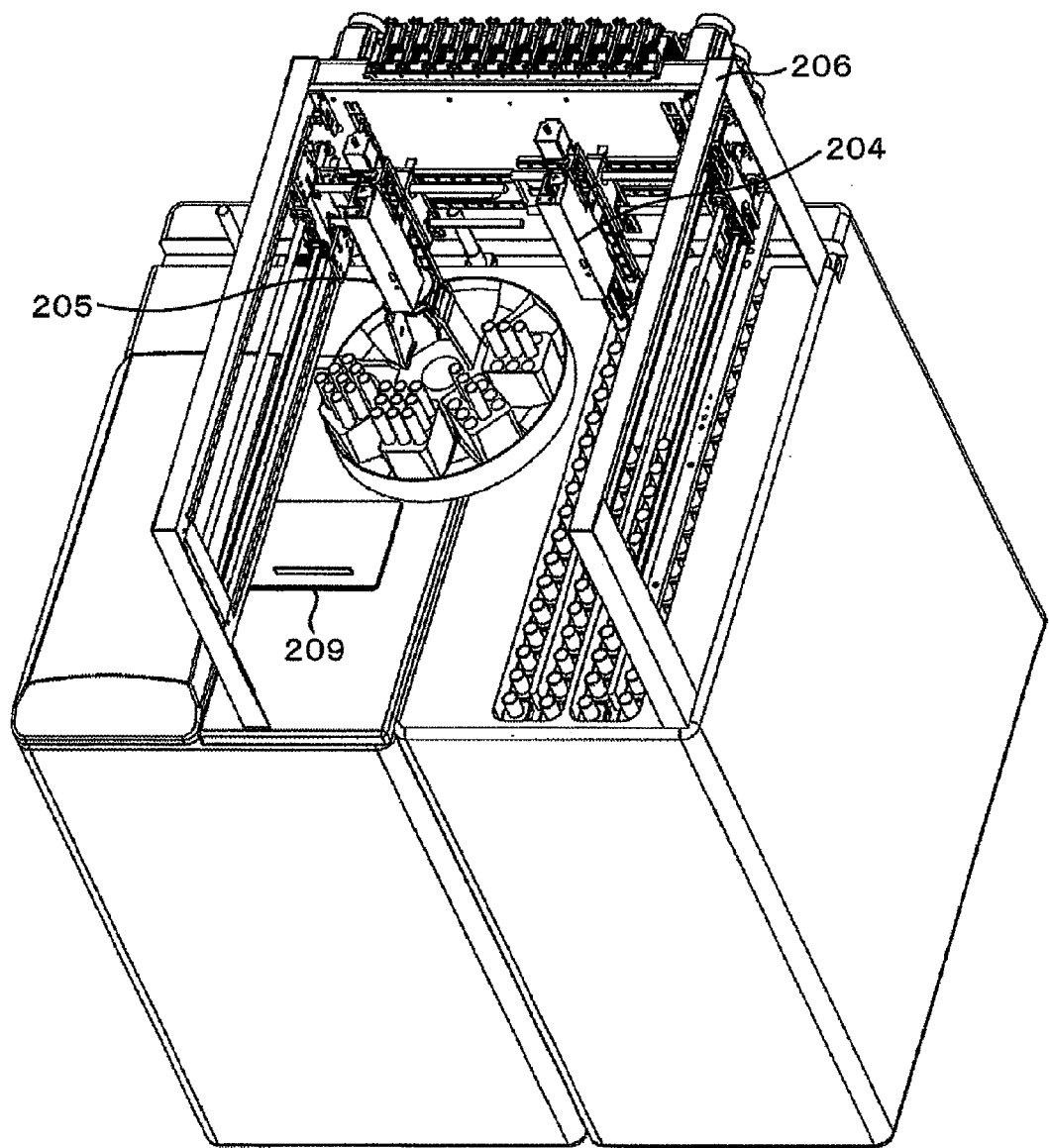
FIG. 3 is a perspective view of an overall configuration of an automatic centrifugal processing unit.
Figure 4:
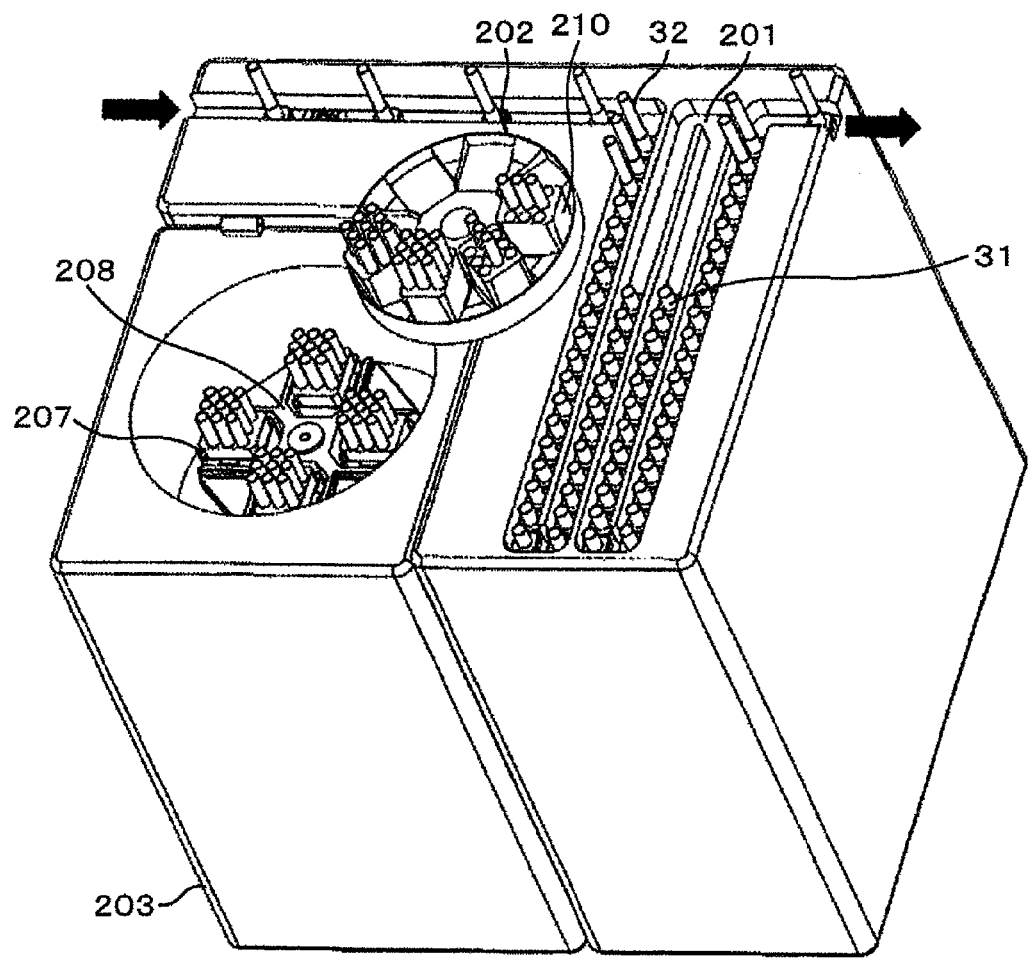
FIG. 4 is a perspective view obtained by removing an upper portion of the automatic centrifugal processing unit.

FIG. 3 illustrates a perspective view of an overall configuration of the centrifugal processing unit according to the present invention among the above-described processing modules, and FIG. 4 illustrates a perspective view from which an upper part thereof is removed.

Main components of the centrifugal processing unit include: a centrifugal buffer line 201 on which a plurality of specimen containers 32 are temporarily stood by; a turn table 202 which holds the adaptor 210; and an automatic centrifuge 203 which centrifuges the specimen. The centrifugal processing is performed while the adaptor 210 is held by the bucket inside the turn table. The lateral sides of the bucket are held by a bucket supporting shaft 01. Therefore, when the turn table 202 is rotated, the adaptor held by the bucket is supported so that a bottom portion of the specimen container is directed toward an outside of the turn table 202 and so that an opening portion of the specimen container is tilted toward a rotation central axis of the turn table 202.

The specimen containers 32 are sequentially conveyed by a belt line from a previous-process unit into a centrifugal buffer line 201 one by one while being supported by the holders 31. The holders 31 sequentially continue the conveying to a center of the centrifugal buffer line. At a position where the specimen container 32 can be removed from the holder 31, the specimen container 32 is transferred to the adaptor 210 on the turn table 202 by a specimen chuck mechanism 204.

It is desired that the number of adaptors which is twice the number of buckets or larger which can be subjected to the centrifugal processing by the automatic centrifuge 203 at once can be installed on the turn table 202. In the present embodiment, since the number of buckets which are subjected to the centrifugal processing by the automatic centrifuge 203 at once is four, eight which is twice the number is described as the number of adaptors. In this manner, by utilizing the waiting time during the centrifugal operation inside the automatic centrifuge 203 (generally, the centrifugal time is 5 to 10 minutes), the specimen container can be transferred from the holder 31 to the adaptor 210 or the operation for the specimen return from the adaptor 210 to the holder 31 can be performed, so that reduction in the throughput of the entire process can be prevented.

The turn table 202 has a rotary drive motor, and rotates while installing the adaptor 210, and is controlled so as to stop at an arbitrary position.

The specimen chuck mechanism 204 is fixed to an XYZ mechanism 206 which is movable in a horizontal direction and a vertical direction, and transfers the specimen between the holder 31 and the adaptor 210. As similar to the specimen chuck mechanism 204, this XYZ mechanism 206 has an adaptor chuck mechanism 205 which conveys the adaptor 210 into the bucket of the automatic centrifuge.

The automatic centrifuge 203 has: a high-speed-rotation drive motor for the centrifugation although not illustrated; a rotor 208 attached to this motor; and a plurality of buckets 207 attached symmetrically to each other across the rotation central axis of the rotor 208.

After the transferring operation of the specimen container 32, which is to be subjected to the centrifugal processing, to the adaptor 210 is completed, the adaptor 210 is inserted into the bucket 207 by the adaptor chuck mechanism 205 while placing the specimen container 32 thereon. After the operations for inserting the adaptors 210 into all the buckets 207 is completed, a safety shutter 209 is closed, then, the centrifugal operation is started. During the centrifugal operation, the operations for removing the specimen container 32 from the holder 31 and inserting the container into the adaptor 210 are continued as preparation for the centrifugal operation in a next cycle. After the centrifugal operation is completed, a reverse process to the above-described operations is promoted. First, the safety shutter 209 is opened, and the adaptor 210 is returned from the bucket 207 to the turn table 202 by the adaptor chuck mechanism 205.

In order to shorten the waiting time of the automatic centrifuge 203, it is desired to return all the adaptors 210 for which the centrifugation operation has been completed to the turn table 202 and to continuously insert the adaptor 210 for the next centrifugal operation into the bucket 207. In order to minimize a return distance from the adaptor 210 to the holder 31, the turn table 202 is rotated. After the turn table 202 stops, the specimen container is returned from the specimen adaptor 210 to the holder 31 by the specimen chuck mechanism 204. The specimen container 32 returned to the holder 31 is conveyed to a next process by the belt line.

First Embodiment

Figure 5:
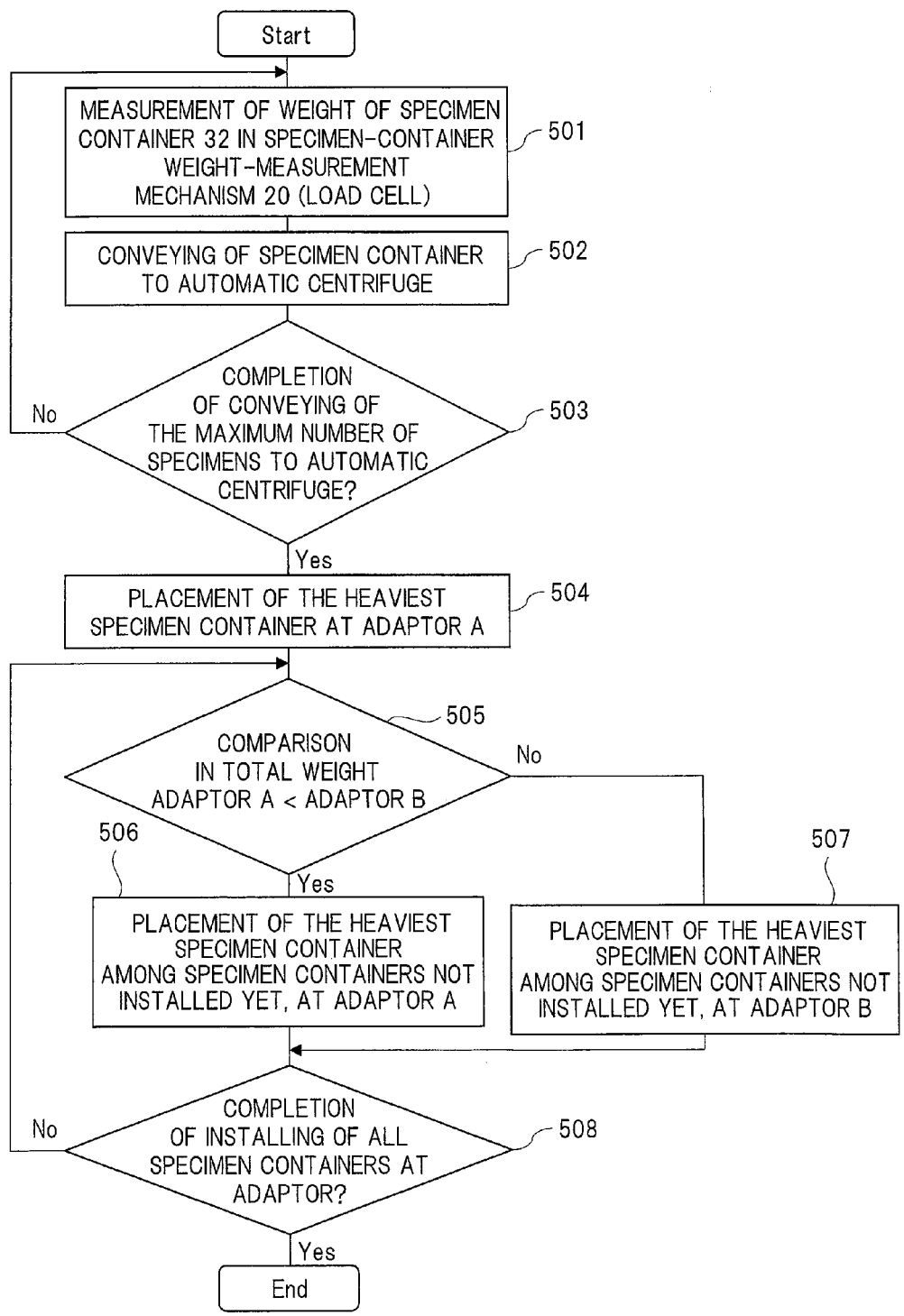
FIG. 5 is a processing flow chart for setting specimens at adaptors of an automatic centrifuge.

FIG. 5 illustrates a process flow from the loading of the specimens to the setting of the specimens at the adaptors 210 of the automatic centrifuge.

For the specimens loaded from the loading module 102, the weight of the specimen container 32 is measured while being set in the holder 31 by a specimen-container weight-measurement mechanism 20 on the main conveyor line 11 in a step 501, and the specimen container is conveyed to the automatic centrifuge in a step 502. The specimen chuck mechanism 204 stands by without setting the specimen container 32 at the adaptor 210 until the number of the specimen containers 32 conveyed to the automatic centrifuge reaches the maximum number of specimens which can be subjected to the centrifugal processing at once (in a step 503).

In order to achieve efficient processing, even if the number does not reach the maximum number of specimens which can be subjected to the centrifugal operation at once but if the next specimen container is not conveyed even after a certain period of waiting time, the conveying to the adaptor may be started in the order from the heaviest one at the moment among the specimens standing by on the centrifugal buffer line 201.

After the maximum number of the specimens which can be subjected to the centrifugal processing is conveyed to the automatic centrifuge, the heaviest specimen container among all of the specimen containers conveyed into the automatic centrifuge is set at an adaptor A (in a step 504) in assumption that the above-described adaptors 210 placed on the pair of buckets positioned symmetrically to each other across the centrifugation rotation center of the rotor are adaptors A and B. After that, the total weights of the adaptor A and the adaptor B are compared with each other in a step 505, the heaviest specimen container among the specimen containers is set at the adaptor A if the adaptor A is lighter in a step 506, and the heaviest specimen container among the specimen containers is set at the adaptor B if the adaptor B is lighter in a step 507. Until setting of all the specimen containers is completed in step 508, step 505 to step 507 are repeated.

Figure 1:
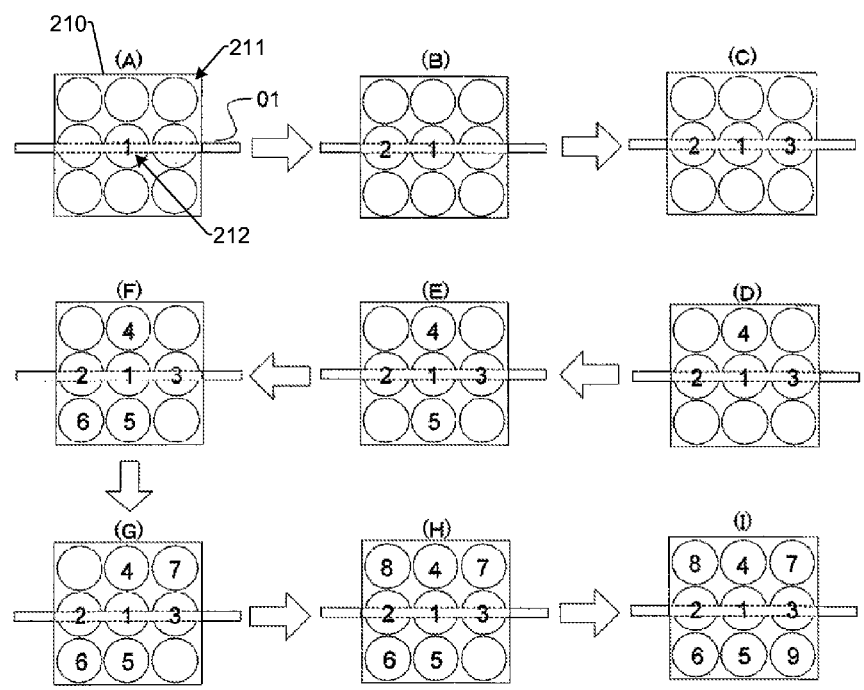
FIG. 1 is a drawing illustrating a setting order of specimen containers at an adaptor.

Also, when the first specimen container is set at the adaptor A, the specimen is set at an installation position close to the gravity center of the adaptor A first. The specimen subsequent to that is alternately set in the order from the inside at a position which is a point of symmetry across the center of the adaptor. FIG. 1 illustrates the setting order of the specimen containers at the adaptor in a case that the number of specimens set at the adaptor is nine as an example.

First, in the step 504, the heaviest specimen container on the centrifugal buffer line is selected, and is installed at a center position of the specimen installation positions of the adaptor A (which is a position 1 of FIG. 1-A).

In the step 505, the total weights of the adaptor A and the adaptor B are compared with each other, and it is determined which adaptor the next heaviest specimen container is to be installed at. In the present embodiment, for example, if the total weight of the adaptor B is lighter, the next specimen is installed at the position 1 of the adaptor B in the step 507.

As described above, the total weights of the adaptor A and the adaptor B are compared with each other, and the heavier specimen container is sequentially installed at the adaptor. Hereinafter, only the specimen containers to be installed at the adaptor A will be focused on, and the installation positions for the specimen containers will be explained.

After the position 1, the next specimen container is installed at either a position 2 or a position 3 as the position having the short distance from the position 1 which is the center position of the adaptor. In the present embodiment, it is assumed that the specimen containers are installed in the order of the position 2, the position 3, the position 4, and the position 5. As to the positions 4 and 5, note that it does not matter that the specimen container is set at either one of them first. Also, in the installation of the third specimen container, the third specimen container is set at a position which is a point of symmetry with respect to the second specimen container across the center (the first specimen container). Similarly, in the installation of the fifth specimen container, the specimen container is set at a position which is a point of symmetry with respect to the fourth specimen container across the center.

Then, the specimen container is installed at any of positions 6 to 9 as a position having a long distance from the position 1. While the specimen containers are installed in the order of the position 6, the position 7, the position 8, and the position 9 in the present embodiment, other orders may be employed. Further, in the installation of the seventh specimen container, the seventh specimen container is set at a position which is a point of symmetry with respect to the sixth specimen container across the center. Similarly, in the installation of the ninth specimen container, the ninth specimen container is set at a position which is a point of symmetry with respect to the eighth specimen container across the center.

In a case that the specimens are installed at the adaptor B, it is desired that the installation positions for the specimen containers are symmetric across the rotation axis of the rotor. For example, in a case that the adaptor A is in the (B) state in FIG. 1 and the adaptor B is in the (A) state in FIG. 1, when the specimen container is to be installed at the adaptor B in a next turn, it is preferred to install the specimen at an installation position which is a position symmetrically to the position 2, that is, at the position 3. Also, in a case that the adaptor A is in the (D) state in FIG. 1 and the adaptor B is in the (C) state in FIG. 1, when the specimen container is to be installed at the adaptor B in a next turn, it is preferred to install the specimen container at a position symmetrically to the position 4 across the rotor rotation axis, that is, at the position 5. By installing the specimen containers as described above, the stable rotation can be achieved even if the conveying of the specimen container to the adaptor is started before the specimen containers are conveyed into the centrifugal buffer line 201 so that the number thereof is the maximum number of the specimen containers which can be installed at the pair of buckets, since the gravity-center positions of the pair of buckets are the symmetric positions to each other across the rotor rotation axis.

In the present embodiment, the case in which the two buckets of the adaptors A and B are provided is described. However, the present invention can be applied to even an automatic centrifuge in which two or more buckets can be subjected to the centrifugal processing. If the difference in the weight between the buckets positioned symmetrically to each other across the rotor rotation axis is not large, the stable centrifugal operation can be achieved, and therefore, the specimen containers are installed at the pair of buckets of the bucket A and the bucket B positioned symmetrically to each other across the rotor rotation axis first while balancing their weights, and then, the specimen containers are installed at other pair of buckets (bucket C and bucket D) positioned symmetrically to each other across the rotor rotation axis while balancing their weights. By sequentially installing the specimen containers at the pair of buckets as described above, the present invention can be also applied to a case of many buckets.

By the above-described technique of setting the adaptors, the total weights of the respective adaptors 210 are compared with each other, and the installation locations are determined, and then, the specimen containers are set in the order from the heavier specimen container. In this manner, the weight added to the total weight of the adaptors 210 is gradually reduced, and therefore, the heavy test tubes are not allocated at the end, and the difference in the weight between the adaptors 210 is difficult to cause. Also, by setting the heavy specimen at the center of the adaptor 210 and setting the light specimen at the outside of the adaptor 210, the shift of the gravity center of the adaptor 210 itself can be prevented, the rotation abnormality of the rotor during the centrifugal processing is suppressed, and the stable centrifugal processing can be performed.

A technique of directly measuring the weight by the weight measurement mechanism is employed to the present invention. However, it is conceivable to obtain the weight of the housed specimen by a technique other than this. For example, a technique of calculating the weight by providing a CCD camera or others on a lateral side of the conveyor line and detecting a liquid level in the specimen container installed in the passing specimen holder may be employed.

Second Embodiment

A process flow according to another embodiment from the loading of the specimens to the setting of the specimens at the adaptors 210 of the automatic centrifuge will be explained.

Here, a case that two automatic centrifuges each of which is one of the pre-analysis units are connected to the pre-analysis system will be explained as an example. Hereinafter, the automatic centrifuges will be referred to as an automatic centrifuge 1 and an automatic centrifuge 2, respectively.

After the bar-code information of the specimen is read in the loading module 102, the weight of the specimen container 32 is measured by the specimen-container weight-measurement mechanism 20 on the main conveyor line 11 while being set at the holder 31. The present weight information is transmitted to the control computer 41 together with the ID of the holder at which the specimen is set.

From the specimen weight, the control computer 41 determines which adaptor 210 the specimen is to be set at, among the adaptors 210 to be paired in the plurality of connected automatic centrifuges. Upon the first specimen recognition, no specimen is placed at the adaptors 210 of either of the automatic centrifuges, and therefore, the specimen container 32 is placed at the adaptor 210 (here, referred to as an adaptor A) of the automatic centrifuge 1, and then, the specimen container 32 is then placed at the adaptor 210 (here, referred to as an adaptor B) to be paired with the adaptor A in the automatic centrifuge 1. Subsequently, in each specimen, the specimen container 32 is set at the adaptor whose total weight is lighter among the adaptor A and the adaptor B. First, among the automatic centrifuge 1 and the automatic centrifuge 2, the specimen containers 32 are set at only the adaptors 210 of either one of the automatic centrifuges. This is because TAT (Turn-Around-Time) of each specimen is shorter when many specimen containers 32 are installed at the adaptors of one of the automatic centrifuges as soon as possible to start centrifugal processing.

Figure 6:
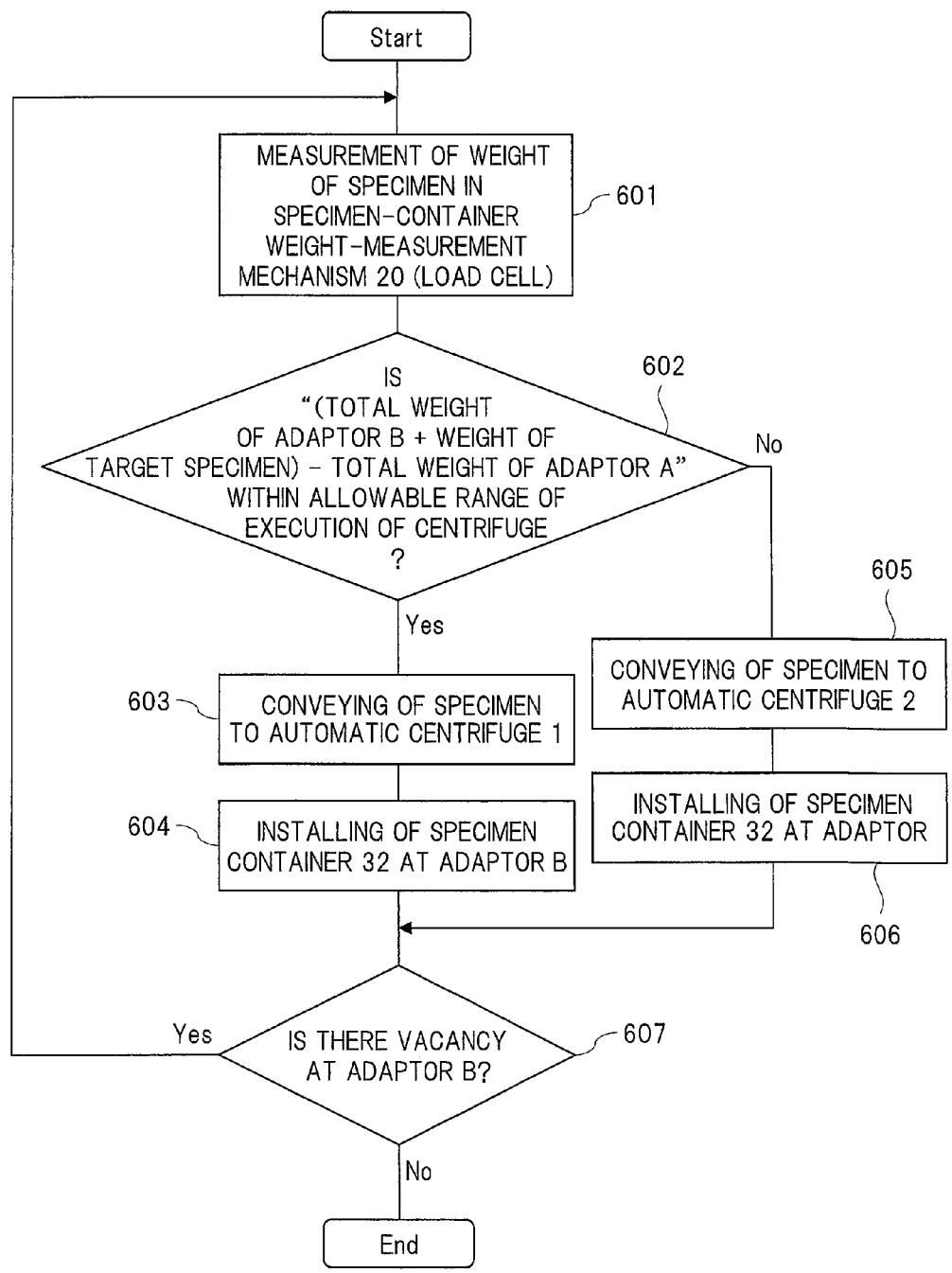
FIG. 6 is a processing flow chart for setting specimens at adaptors of an automatic centrifuge.

Here, a technique of determining the specimen setting adaptors will be explained below in a case that the specimen containers are set at all the specimen installation positions of either one of the adaptor A and the adaptor B of the automatic centrifuge 1 and that the setting can be achieved at the other adaptor. In FIG. 6, a case that the adaptor B has the vacancy so that specimen container can be set thereat after the specimen containers are set at the entire of the adaptor A will be explained as an example.

In a step 601, the weight of the specimen container 32 is measured by the specimen-container weight-measurement mechanism 20 on the main conveyor line 11 while being set at the holder 31. In a step 602, For the specimen container to be set at the adaptor at this time, the value obtained by adding the specimen weight measured by the specimen-container weight-measurement mechanism 20 to the total weight of the adaptor B having the vacancy is compared with the total weight of the adaptor A. If the difference in the weight therebetween allows the centrifugal processing, the specimen is conveyed to the automatic centrifuge 1 in a step 603, and the specimen container 32 is set at the adaptor B in a step 604.

However, if the difference in the weight does not allow the centrifugal processing, there is a possibility that the centrifugal processing is abnormally performed by setting the specimen at the adaptor B. Accordingly, the specimen is conveyed to the other automatic centrifuge 2 in a step 605, and the specimen is set at the adaptor A' 210 of the second automatic centrifuge 2 in a step 606. In this case, since the adaptor B of the automatic centrifuge 1 has the vacant position at which the specimen container can be installed, the process in a step 607 returns to the step 601 again, it is determined whether the specimen container 32 whose weight has been measurement next can be set at the adaptor B or not in the step 602, and the processes are repeated until the specimen which can be set at the adaptor B is found.

By the above-described technique, the difference in the weight between the adaptors to be paired in the automatic centrifuge is minimized, so that the centrifugal processing can be normally performed, and besides, the specimen can be continuously set at the adaptor having the vacancy as long as the difference in the weight allowing to execute the centrifugal processing, so that the reduction of the processing performance can be prevented.

Although not illustrated in the process flow, at the point when the conveying of the specimen container to the automatic centrifuge 2 is determined in the step 605, note that the centrifugal processing may be started by putting the priority on the TAT of each specimen so as to end the setting of the specimen at the adaptor 210 of the automatic centrifuge 1, or the centrifugal processing of the automatic centrifuge 1 may be started at a moment when the number of counts of the generation of the specimens which cannot be set at the adaptor B in the step 602 exceeds a predetermined number of counts.

Third Embodiment

Next, a procedure according to still another embodiment from the loading of the specimen, then, the recognition of the abnormal specimen, until the collection of the specimen will be explained.

Prior to the start of the pre-analysis processing, the normal-specimen weight range values are set. FIG. 7 illustrates an example of a setting screen of the normal-specimen weight range values of each specimen container. In FIG. 7, the minimum weight and the maximum weight are set for each test tube container. Also, in an item "Others" in FIG. 7, a value used when a specimen container whose shape cannot be determined by a shape recognition mechanism of the specimen container 32 is loaded into the system is set.

When the specimen container 32 is loaded by the loading module 102, the specimen container 32 is transferred to the holder 31, and the conveying is started. For the specimen container 32, the container shape is recognized by means for recognizing the specimen container shape (here, it is assumed that a 16ϕ 100-mm test tube has been recognized).

Next, the weight of the specimen container 32 is measured by the specimen-container weight-measurement mechanism 20 (it is assumed that the measured weight of the specimen container is 7 g). Then, from the recognized test tube shape, the normal-specimen weight range value is determined (in FIG. 7, the normal-specimen weight is 10 g to 30 g). As the normal-specimen weight range value, it is conceivable to set, for example, a range from a liquid volume minimally required for dispensing the specimen required for analysis from the test tube by a dispensing nozzle to a some liquid volume which does not result in liquid scattering or spill out in the processing and conveying of the specimen with the test tube. The measured weight of the specimen container is compared with the normal-specimen weight range value set for the test tube. If the weight is out of the set normal-specimen weight range value (as the present example), the abnormality in the specimen is determined, and the specimen container is collected directly to the housing module 103. If it is within the normal-specimen weight range value, it is determined that a normal specimen volume is contained in the container, and then, the specimen container is conveyed to the pre-analysis module based on the category information of the specimen.

Also, it is desired to provide alert means for alerting an operator if the specimen determined as the abnormality in the specimen is generated. As a technique of the alert, it is conceivable to provide a dedicated screen display on an operation screen. Through the screen display, the operator can be encouraged to perform the addition for the lack of the specimen or the reset for an appropriate specimen volume. Also, as another technique of the alert, a technique of alerting the operator to the generation of the abnormality in the specimen by light or sound is conceivable. In this case, an operator at a distance can be also alerted of the generation of the abnormality in the specimen.

By the present means, the abnormal specimen can be recognized at an early stage of the specimen loading, and the specimen can be loaded outside the device. In this manner, the user checks the state of the specimen which has been recognized as the abnormal specimen, takes such an action as the addition of the specimen, and reloads it, so that the result report delay can be minimized.

Fourth Example

Next, a procedure for measuring the correct specimen weight according to still another embodiment will be explained.

First, maintenance for performing holder weight measurement is executed. When the holder-weight measurement maintenance is executed, the system conveys the holder 31 which is standing by in the rack stocker 101, to the specimen-container weight-measurement mechanism 20 by the vacant-rack conveyor lines 14a and 14b. For the holder 31 conveyed to the specimen-container weight-measurement mechanism 20, a weight of a single body of the holder is measured. The weight of the holder measured at this time is stored. A storing technique may be performed by attaching a storage medium such as an RFID to the holder 31 to store the weight in the holder 31 itself or by pasting a barcode onto the holder 31 and transmitting the weight to the control computer 41 together with the barcode information upon the weight measurement for the storage. After the weight measurement, the holder 31 is stored in the rack stocker 101 through the vacant-rack conveyor lines 14a and 14b.

Next, a procedure from the loading of the specimen into the system to the calculation of the specimen container weight will be explained.

The specimen container 32 is loaded into the loading module 102, the specimen container 32 is transferred to the holder 31, and the conveying into the pre-analysis system is started. While the conveyed specimen container 32 is set at the holder 31, the total weight of the specimen container 32 and the holder 31 is measured by the specimen-container weight-measurement mechanism 20. Also, the weight of the specimen is calculated by reading the RFID or the barcode attached to the holder 31, retrieving the weight of the holder 31 itself previously measured in the holder weight measurement maintenance, and subtracting the previously-measured holder weight from the measured weight.

The holder weight is varied by the machining accuracy. Also, there is a possibility of change in the weight of the holder itself due to usage for a long period of time. Therefore, the correct specimen weight can be always measured by using a new holder or by regularly measuring the holder weight by the present technique, and, as a result, the setting adaptor of the automatic centrifuge is determined by using the weight, which results in the stable operation of the centrifugal processing.

SYMBOL EXPLANATION bucket supporting shaft
11 main conveyor line
12 emergency overtaking line
13 return line
14a and 14b vacant-rack conveyor line
16 and 17 branch line
20 specimen-container weight-measurement mechanism
22 conveyor line
31 holder
32 specimen container
33 tray
41 control computer
51 host computer
101 rack stocker
102 loading module
103 housing module
104 and 105 processing module
201 centrifugal buffer line
202 turn table
203 automatic centrifuge
204 specimen chuck mechanism
205 adaptor chuck mechanism
206 XYZ mechanism
207 bucket
208 rotor
209 safety shutter
210 adaptor
211 hole
212 center

The invention claimed is:

1. A pre-analysis system comprising:
a conveyor line which conveys a plurality of holders for holding a first plurality of specimen containers in which respective specimens are housed;
an automatic centrifugal unit arranged along the conveyor line; and
a computer connected with the conveyor line and the automatic centrifugal unit;
the automatic centrifugal unit comprising:
  a centrifuge which rotates a second plurality of specimen containers around a rotation central axis;
  a plurality of adaptors, each of which has a plurality of holes, configured in a lattice pattern, each hole able to receive a respective specimen container of the first plurality of specimen containers;
  a plurality of buckets positioned symmetrically to each other across the rotation central axis of the centrifuge and on which the adaptors can be installed detachably; and
  a specimen container chuck mechanism fixed on a horizontal and vertical transporting mechanism;
wherein the computer is programmed to control the specimen container chuck mechanism to:
  grip one of the specimen containers held in one of the holders,
  transport of the specimen container gripped by the specimen container chuck mechanism from the one of the holders to the adaptor, and
  install the specimen containers gripped by the specimen container chuck mechanism into respective holes of the adaptor sequentially in an order from a hole arranged in the lattice pattern closer to a gravity center of the adaptor and, concurrently, in an order from a heavier specimen container to a lighter specimen container.

2. The pre-analysis system according to claim 1, wherein:
the automatic centrifugal unit further comprises:
  a buffer line that is adjacent to the conveyor line and that holds a number of the specimen containers; and
  a weight determination mechanism which directly or indirectly obtains a weight of the respective specimen housed in the respective specimen container prior to loading of the respective specimen container into a holding region on the automatic centrifugal unit; and
the computer is further programmed to control the specimen container chuck mechanism to install the specimen containers at the buffer line based on information obtained by the weight determination mechanism.

3. The pre-analysis system according to claim 1, wherein the automatic centrifugal unit further comprises a buffer line that is adjacent to the conveyor line, wherein the buffer line can hold a number of the specimen containers that is equal to or larger than the number of the specimen containers that can be installed at the plurality of adaptors at once.

4. The pre-analysis system according to claim 1, wherein the automatic centrifugal unit includes:
an adaptor holding unit which holds a plurality of the adaptors; and
an adaptor transferring mechanism which transfers the adaptors from the adaptor holding unit to the bucket and transfers the adaptors from the bucket to the adaptor holding unit, wherein:
  the adaptor transferring mechanism is provided separately from the specimen container chuck mechanism, and
  the adaptor holding unit holds a number of the adaptors that is larger than a number of the adaptors which can be processed by the automatic centrifugal unit at once.

5. The pre-analysis system according to claim 2, further comprising a specimen collecting unit which collects a specimen container whose specimen container weight determined by the weight determination mechanism is out of a predetermined range of a threshold value.

6. The pre-analysis system according to claim 5, further comprising a display device which displays a setting screen for setting the threshold value of the specimen container weight so as to correspond to a type of the specimen container.

7. An automatic centrifuge comprising:
a centrifuge that rotates a plurality of specimen containers around a rotation central axis;
at least two adaptors which have a plurality of holes in which a plurality of specimen containers can be installed;
at least two buckets positioned symmetrically to each other across the rotation central axis of the centrifuge in which the adaptors can be installed;
a buffer line which holds a number of the specimen containers;
a specimen container chuck mechanism configured to convey at least some of the specimen containers held in the buffer line to the adaptors; and
a computer connected with the centrifuge, the buffer line, and the specimen container chuck mechanism, wherein the computer is programmed to control the specimen container chuck mechanism to install the specimen containers sequentially in an order from a hole closer to a gravity center of the adaptor and, concurrently, in an order from a heavier specimen container to a lighter specimen container.

8. The automatic centrifuge according to claim 7, wherein:
the automatic centrifuge includes a weight determination mechanism which directly or indirectly obtains a weight of the specimen housed in the specimen container prior to loading of the specimen container into a holding region; and
the computer is further programmed to control the specimen container chuck mechanism so that the specimen containers are installed at the adaptor based on information obtained by the weight determination mechanism.

9. The automatic centrifuge according to claim 7, wherein the buffer line can hold a number of the specimen containers that is larger than a number of the specimen containers that can be installed at the plurality of adaptors at once.

10. The automatic centrifuge according to claim 7 further comprising:
an adaptor holding unit which holds a plurality of the adaptors; and
an adaptor transferring mechanism which transfers the adaptors from the adaptor holding unit to the bucket and transfers the adaptors from the bucket to the adaptor holding unit, wherein:
the adaptor transferring mechanism is provided separately from the specimen container chuck mechanism, and
the adaptor holding unit holds a number of the adaptors that is larger than a number of the adaptors that can be processed by the automatic centrifugal unit at once.

11. The pre-analysis system according to claim 1, wherein the computer is further programmed to control the specimen container chuck mechanism to:
install a first specimen container into a first hole of the adaptor that is positioned closest to the gravity center of the adaptor;
install a second specimen container into a second hole of the adaptor that is positioned second closest to the gravity center of the adaptor; and
install a third specimen container into a third hole of the adaptor that is positioned symmetrically to the gravity center of the adaptor with respect to the second hole.

12. The pre-analysis system according to claim 1, wherein the plurality of holes of the adaptor include a centrally located hole at the gravity center of the adaptor and a plurality of other holes symmetrically arranged around the centrally located hole to provide the lattice pattern.

13. The automatic centrifuge according to claim 7, wherein the computer is further programmed to control the specimen container chuck mechanism to:
install a first specimen container into a first hole of the adaptor that is positioned closest to the gravity center of the adaptor;
install a second specimen container into a second hole of the adaptor that is positioned second closest to the gravity center of the adaptor; and
install a third specimen container into a third hole of the adaptor that is positioned symmetrically to the gravity center of the adaptor with respect to the second hole.

14. The automatic centrifuge according to claim 7, wherein the plurality of holes of the adaptor are arranged in a lattice pattern.

15. The automatic centrifuge according to claim 14, wherein the plurality of holes of the adaptor include a centrally located hole at a gravity center of the adaptor and a plurality of other holes symmetrically arranged around the centrally located hole to provide the lattice pattern.

16. A system comprising:
a centrifuge configured to rotate a plurality of specimen containers around a rotation central axis;
at least two adaptors, each adaptor having a plurality of holes configured to receive respective specimen containers, the plurality of holes including a centrally located hole at a gravity center of the adaptor and a plurality of other holes symmetrically arranged around the centrally located hole;
at least two buckets positioned symmetrically to each other across the rotation central axis of the centrifuge into which the adaptors can be installed;
a buffer line able to hold a number of the specimen containers;
a specimen container chuck mechanism configured to convey at least some of the specimen containers held in the buffer line to the adaptors; and
a computer connected with the centrifuge, the buffer line, and the specimen container chuck mechanism, wherein the computer is programmed to control the specimen container chuck mechanism to install the specimen containers sequentially in an order from the centrally located hole at the gravity center of the adaptor and, concurrently, in an order from a heavier specimen container to a lighter specimen container based at least partially on comparing respective weights of the specimen containers.

17. The system according to claim 16, wherein during the installing of the specimen containers, the computer is further programmed to control the specimen container chuck mechanism to install the specimen containers into two adapters concurrently by selecting one of the two adapters having a lightest total weight to receive a next specimen container, wherein the specimen containers are installed into each of the two adapters based on the order from respective centrally located holes and the order based at least partially on comparing respective weights of the specimen containers.

18. The system according to claim 17, wherein the computer is further programmed to determine a heaviest remaining specimen container to be installed into one of the two adaptors and select the heaviest remaining specimen container as the next specimen container.

19. The system according to claim 16, wherein the plurality of holes of the adaptor are arranged in a lattice pattern.

* * * * *